(12) United States Patent
Shanklin et al.

(10) Patent No.: US 7,115,273 B2
(45) Date of Patent: Oct. 3, 2006

(54) ANTI-VIRAL LOTION TISSUE, AND METHODS FOR MAKING AND USING THE SAME

(75) Inventors: Gary L. Shanklin, Fremont, WI (US); Duane G. Krzysik, Appleton, WI (US); Cynthia W. Henderson, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 757 days.

(21) Appl. No.: 09/753,136

(22) Filed: Dec. 29, 2000

(65) Prior Publication Data

US 2002/0006434 A1 Jan. 17, 2002

Related U.S. Application Data

(60) Provisional application No. 60/173,830, filed on Dec. 30, 1999.

(51) Int. Cl.
*A01N 25/10* (2006.01)

(52) U.S. Cl. .................. 424/404; 424/405; 424/406; 514/557; 514/887

(58) Field of Classification Search ........... 424/402, 424/409, 404–406; 514/557, 887
See application file for complete search history.

(56) References Cited

U.S. PATENT DOCUMENTS

| | | | |
|---|---|---|---|
| 4,738,847 A | 4/1988 | Rothe et al. | |
| 4,764,418 A | 8/1988 | Kuenn et al. | |
| 4,772,501 A | 9/1988 | Johnson et al. | |
| 4,824,689 A | 4/1989 | Kuenn et al. | |
| 4,828,912 A | 5/1989 | Hossain et al. | |
| 4,897,304 A | 1/1990 | Hossain et al. | |
| 4,908,262 A | 3/1990 | Nelson | |
| 5,049,440 A | 9/1991 | Bornhoeft, III et al. | |
| 5,705,164 A * | 1/1998 | Mackey et al. | 424/400 |
| 5,720,966 A | 2/1998 | Ostendorf | |
| 5,830,487 A | 11/1998 | Klofta et al. | |
| 5,833,961 A | 11/1998 | Siegfried et al. | 424/59 |
| 5,869,075 A | 2/1999 | Krzysik | |
| 5,871,763 A * | 2/1999 | Luu et al. | 424/402 |
| 5,989,527 A * | 11/1999 | Siegfried et al. | 424/59 |

* cited by examiner

*Primary Examiner*—Neil S. Levy
(74) *Attorney, Agent, or Firm*—Brinks Hofer Gilson & Lione

(57) ABSTRACT

A soothing anti-viral lotion composition and a lotioned tissue product having a surface with the lotion composition applied thereto, and methods for making and using the same. The lotion composition includes an anti-viral organic acid and a topical delivery system. The topical delivery system includes one or more polyesters which allow incorporation of the organic acids into the lotion formulation, controls their delivery, and maintains them in the stratum corneum. The lotion composition may optionally contain a surfactant, an irritation inhibiting agent, and other additives.

8 Claims, No Drawings

ANTI-VIRAL LOTION TISSUE, AND METHODS FOR MAKING AND USING THE SAME

RELATED APPLICATIONS

This application is a continuation of U.S. App. Ser. No. 60/173,830, entitled, "Anti-Viral Lotion Tissue, and Methods for Making and Using the Same," filed Dec. 30, 1999, the entire disclosure of which is incorporated herein by reference.

FIELD OF THE INVENTION

The present invention relates generally to anti-viral lotion composition and a lotioned tissue having anti-viral properties. More specifically, the present invention relates to a composition and a lotioned tissue including a surface having an anti-viral organic acid and a topical delivery system applied thereto, and methods for making and using the same.

BACKGROUND

Various types of anti-viral tissues are known in the art. U.S. Pat. No. 5,830,487, issued to Klofta et al., discloses a lotioned tissue paper having an anti-viral lotion composition that is a semi-solid or solid at 20° C. The lotion comprises an organic acid, a hydrophilic solvent, an emollient, an immobilizing agent, a nonionic surfactant, an oil and other additives.

U.S. Pat. No. 5,705,164, issued to Mackey et al., discloses a tissue paper having a lotion composition that is a solid or semisolid at room temperatures. The lotion composition may include an emollient, preferably a liquid polyol polyester, used to soften, sooth, or moisturize the skin, and may include oils and fatty alcohols, and an immobilizing agent which also may contain polyesters. Other optional components include water, skin soothing agents, or anti-inflammatories such as aloe vera or panthenol, and disinfectant antibacterial actives.

U.S. Pat. No. 5,871,763, issued to Luu et al., discloses substrates such as a tissue or towel which are treated with a lotion. The lotion provides a smooth feel that is lubricious and nongreasy, and is a solid at room temperature. The lotion may include an emollient such as a fat, oil, phospholipid, silicone, esters, or mixtures of esters; a retention agent; conventional surfactants, including cationic surfactants; anti-viral agents, including organic acids, a fragrance, a powder, an extract; and/or a humectant.

U.S. Pat. No. 5,720,966, issued to Ostendorf, discloses a tissue paper having a semisolid therapeutic composition comprising a medicinal component such as a virucide, disinfectant or analgesic and a lotion, which preferably includes mineral oil, paraffin wax, cetearyl alcohol, aloe extract and steareth-2.

U.S. Pat. No. 5,049,440, issued to Bornhoeft, III et al., discloses a wet wiper having a liquid preservative composition including water, a naturally occurring organic acid and a naturally occurring salt. The wet wipe may also contain fragrances and skin moisturizers such as glycerine, aloe vera, lecithin, lanolin, and lanolin derivatives.

U.S. Pat. No. 4,772,501, issued to Johnson et al., discloses a wet wipe product in the form of a fibrous wipe. The wipe has a liquid preservative composition having a mixture of citric and sorbic acids, and other optional components such as water, skin moisturizers, and fragrances.

U.S. Pat. No. 4,908,262, issued to Nelson, discloses toilet seat covers such as a fibrous sheet in which microencapsulated particles of water-soluble salts, preferably copper salts, and water-soluble ene-diol compounds are entrained. The ene-diol compounds include dihydroxymaleic acid, ascorbic acid and compounds thereof, squaric acid and dehydroxyfumaric acid.

U.S. Pat. No. 5,869,075, issued to Kryzik, discloses a soft tissue product having a hydrophilic composition applied to its surface. The composition includes a polyethylene glycol, a fatty alcohol, and lipophilic emollients. The composition may also incude anti-microbial agents or other additives, such as skin exfoliating agents (alpha hydroxy acids) and cationic surfactants.

U.S. Pat. Nos. 4,828,912 and 4,897,304, both issued to Hossain et al., pertain to the use of a carboxylic acid/surfactant virucidal composition for use in absorbent products. U.S. Pat. Nos. 4,764,418 and 4,824,689, both issued to Kuenn et al., pertain to the addition of water-soluble humectants to carboxylic acid/surfactant virucides for use in tissue products to reduce irritation potential. U.S. Pat. No. 4,738,847 issued to Rothe et al., pertains to adding a carboxylic acid/surfactant virucide to the center ply of a three ply tissue to prevent the transfer of the virucidal composition to the user, and thereby reduce irritation potential.

Despite attempts made in a number of products, irritation caused by anti-viral organic acids in tissue products remains a persistent problem.

SUMMARY

Therefore, there continues to be a need for improvements to lotioned tissues. The present invention provides lotion compositions and tissue products that are effective in killing viruses, but do not irritate the skin.

In one aspect of the invention, a tissue product has at least one surface treated with a lotion composition including an anti-viral organic acid and a topical delivery system including at least one polyester. The lotion composition may also optionally include a surfactant, an irritation inhibiting agent, and other additives such as oils, waxes, and fatty alcohols.

In a further aspect of the invention, a method is provided for making the anti-viral tissue product. In yet another aspect of the invention, a method is provided for using the anti-viral tissue product to inhibit the spread of illness.

Other aspects of the invention will be apparent in view of the following description of the preferred embodiments.

DETAILED DESCRIPTION OF THE PREFERRED EMBODIMENTS

The present invention concerns an improved lotion composition for application to a tissue product, and tissue products having the lotion composition applied to one or more surfaces thereof The present invention is suitable for making tissue products such as facial tissues, bathroom tissues, table napkins, paper towels, and the like.

The present invention also concerns a method of preventing the spread of a viral infection by providing anti-viral lotion tissue product having the lotion composition applied thereto. The user contacts the tissue product to a body part, such as the nose, and some of the lotion is transferred to the user. A fluid containing at least one virus, such as a nasal discharge, is absorbed into the tissue. The anti-viral organic acid contacts the lotion composition on both the tissue and on the user's skin, and the virus is acted upon by the virucide in the lotion composition.

The lotion compositions of the present invention comprise an anti-viral organic acid and a topical delivery system or emollient comprising one or more polyesters. The topical delivery system allows incorporation of the acids into the lotion formulation, controls their delivery, and maintains them in the stratum corneum. This reduces the amount of acid necessary for efficacy, and thereby reduces the potential for irritation. Optional components include surfactants, irritation inhibiting agents, and additives such as oils, waxes, fatty alcohols, humectants, and the like. Each one of these components will be discussed in turn:

1. Anti-viral organic acids

The anti-viral organic acids of the present invention are generally solids or semi-solids at room temperature. Preferred anti-viral organic acids comprise at least one member selected from the group consisting of carboxylic acids having the structure R-COOH, wherein R is a $C_1$–$C_6$ alkyl; $C_1$–$C_6$ alkyl carboxy; $C_1$–$C_6$ alkyl carboxyhydroxy; $C_1$–$C_6$ alkyl carboxy halo; $C_1$–$C_6$ alkylcarboxy dihydroxy; $C_1$–$C_6$ alkyl dicarboxyhydroxy; $C_1$–$C_6$ lower alkenyl; $C_1$–$C_6$ alkenyl carboxy; $C_1$–$C_6$ alkenyl phenyl; or substituted phenyl radical. Especially preferred carboxylic acids are citric, malic, adipic, glutaric, and succinic acids and mixtures thereof In the above compounds one or more of the hydrogen atoms may be substituted by halogen atoms, hydroxyl groups, amino groups, thiol groups, nitro groups, cyano groups, and the like.

Typically, the anti-viral organic acid will comprise from about 1 weight percent to about 25 weight percent of lotion composition. As used herein, a "virucidal effective amount" for each compound will depend on the efficacy of the virucide. One possible way to measure the effective amount of a virucide is the amount sufficient to inactivate 99 percent (2 log drop) of rhinovirus type 16 within 10 minutes. A suitable method for testing virucidal efficacy is the Virucidal Assay Procedure disclosed in U.S. Pat. No. 4,897,304, which is incorporated herein by reference. However, those skilled in the art of virology will recognize other suitable test procedures for this purpose.

2. Topical delivery system

The topical delivery system (or emollient) of the present invention functions to incorporate the anti-viral organic acids into the lotion formulation, controls their delivery, and maintains them in the stratum corneum. This reduces the amount of acid necessary for efficacy, and thereby reduces the potential for irritation.

The topical delivery systems of the present invention comprise one or more polyesters. The polyesters of the present invention can be made from repeating monomeric units, as well as dimers, trimers, or tetramers.

Preferred polyesters include hydroxy-functional polyester diols and fatty alkyl capped complex polyesters. An especially preferred hydroxy-functional polyester diol is trimethylpentanediol/apidic acid copolymer (CAS No. 26139-53-7), sold under the trade name LEXOREZ®TL-8, by the Inolex Chemical Co. of Philadelphia, Pa. An especially preferred fatty alkyl capped complex polyester is trimethylpentanediol/apidic isononanoic acid copolymer (CAS NO. 200512-90-9), sold under the trade name LEXOREZ®T TC-8, also by the Inolex Chemical Co.

Preferably, the topical delivery system will comprise from about 5 weight percent to about 25 weight percent of lotion composition.

3. Surfactant

The lotion compositions of the present invention may also contain a conditioning surfactant. The surfactants function to condition the skin while aiding in the inactivation of certain respiratory viruses.

Preferred cationic surfactants are quaternary ammonium compounds. More preferred cationic surfactants having the general formula:

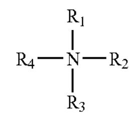

wherein $R_1$, $R_2$, $R_3$, R4 are independently selected from branched or straight chain, saturated or unsaturated $C_1$–$C_6$ or $C_{14}$–$C_{24}$ compounds. No more than three of $R_1$, $R_2$, $R_3$, and R4 may be a $C_1$–$C_6$ alkyl. R3 and R4 may comprise ring structure.

Especially preferred cationic surfactants include stearalkonium chloride;

methyl-1-($C_{12}$–$C_{24}$) amido ethyl-2-($C_{12}$–$C_{24}$) imidazolinium methyl sulfates; $C_{12}$–$C_{24}$ quaternized esteramines; di ($C_1$–$C_6$ alkyl) di ($C_{12}$–$C_{24}$ alkyl) quaternary ammonium methyl sulfates; and polyquaternary cationic compounds.

Preferably, the cationic surfactant will comprise from about 1 weight percent to about 25 weight percent of lotion composition.

4. Irritation inhibiting agents

The lotion compositions of the present invention may also contain an irritation inhibiting agent. The irritation inhibiting agents function to soothe the skin that may be irritated by the other lotion components.

Preferred irritiation inhibiting agents include strontium compounds and silicone glycols. Especially preferred strontium compounds include $Sr^{2+}$ in combination with appropriate counter anions. Inorganic anions include, but are not limited to, nitrate, halogens (particularly F, Cl, Br and I), carbonate, bicarbonate, hydroxide, oxide, peroxide, nitrite, sulfide, bisulfate, persulfate, glycero-phosphate, hypophosphate, borate and titanate. Examples of potentially suitable organic anions include carboxylic acids, alkoxylates, amino acids, peptides, saturated and unsaturated organic acids, and saturated and unsaturated fatty acids. Particular examples include citrate, oxalate, acetate, gluconate, lactate, tartrate, maleate,benzoate, propionate, salicylate, ascorbate, formate, suc-cinate, folinate, aspartate, phthalate, oleate, palmitate, stearate, lauryl sulfate, lanolate, myristate, behenate, caseinate, cyclamate, pantothenate, EDTA and other polyaminopolycarboxylates, saccharin, thioglycolate, laurate, methylparaben, propylparaben, and ricinoleate andsorbate anions.

Preferably, the irritation inhibiting agents will be present in concentrations from about 5.0mM to about 3000mM of lotion composition.

5. Additives

The lotion composition may contain other conventional additives, such as oils, waxes, fatty alcohols, humectants, and the like.

The oils in the lotion composition serve as a carrier for the composition and to enhance skin barrier function. The amount of oil in the composition can be from about 1 to about 95 weight percent. Suitable oils include, but are not limited to, the following classes of oils: petroleum or mineral oils, such as mineral oil and petrolatum; animal oils, such as mink oil and lanolin oil; plant oils, such as aloe extract, sunflower oil and avocado oil; and silicone oils, such as dimethicone and alkyl methyl silicones.

The waxes in the lotion composition function as a melting point control and to restrain lotion composition on the surface of the substrate. The amount of wax in the composition can be from about 5 to about 95 weight percent. Suitable waxes include, but are not limited to the following classes: natural waxes, such as beeswax and carnauba wax; petroleum waxes, such as paraffin and ceresine wax; silicone waxes, such as alkyl methyl siloxanes; or synthetic waxes, such as synthetic beeswax and synthetic sperm wax.

The fatty alcohols in the lotion compositions function to enhance the feel of the lotion and to enhance the lotion's transfer abilities. The amount of fatty alcohol in the composition, if present, can be from about 5 to about 40 weight percent. Suitable fatty alcohols include alcohols having a carbon chain length of $C_{14}$–$C_{30}$, including cetyl alcohol, stearyl alcohol, and dodecyl alcohol.

The humectants in the lotion composition function to stabilize the moisture content of the tissue in the presence of fluctuating humidity. The water-soluble humectant can be any such material or compound which can be applied to the tissue web in a uniform manner, as by spraying, coating, dipping or printing, etc., and which possesses hygroscopic or humectant properties and which will not interfere with the virucidal effectiveness of the tissue product to the extent that the tissue product is no longer virucidally effective. Examples of suitable water-soluble humectants include: polyglycols (as hereinafter defined), propylene glycol, sorbitol, lactic acid, sodium lactate, glycerol, and ethoxylated castor oil.

Polyglycols, which for purposes herein include esters or ethers of polyglycols, having a weight average molecular weight of from about 75 to about 90,000 are suitable for purposes of this invention. This molecular weight range represents physical states ranging from a low viscosity liquid to a soft wax to a fairly hard solid. The higher molecular weight polyglycols naturally have to be melted in order to be applied to a tissue web. Examples of suitable polyglycols include polyethylene glycol, polypropylene glycol, polyoxypropylene adducts of glycerol, methoxypolyethylene glycol, polyethylene glycol ethers of sorbitol, polyethylene glycol ethers of glycerol, polyethylene glycol ethers of stearic acid, polyethylene glycol ethers of lauryl alcohol, citric acid fatty esters, malic acid fatty esters, polyethylene glycol ethers of oleyl alcohol, and ethoxylated stearate esters of sorbitol. Polyethylene glycol is a preferred polyglycol because it can be applied to the tissue in amounts which are effective in improving softness without leaving a noticeable residue on the consumer's hands. Polypropylene glycol is also effective, but tends to leave more of a residue at equivalent amounts and is more hydrophobic than polyethylene glycol.

The amount of water-soluble humectant in a single ply or web of a tissue product of this invention can be about 0.05 to weight percent or greater. The weight percentage amount can vary greatly, depending upon the desired tactile properties, the amount of carboxylic acid present that needs to be counteracted, the properties of the water-soluble humectant itself, etc. At water-soluble humectant levels greater than about 20 weight percent, the tissue product becomes soggy and unacceptable for normal tissue usage. More preferably, the amount of polyglycol in a single ply or web of a tissue product can be from about 2 to about 6 weight percent.

In order to better enhance the benefits to consumers, additional ingredients can be used. The classes of ingredients and their corresponding benefits include, without limitation, vitamins (topical medicinal benefits); dimethicone (skin protection); powders (lubricity, oil absorption, skin protection); preservatives and antioxidants (product integrity); ethoxylated fatty alcohols; (wetability, process aids); fragrance (consumer appeal); lanolin derivatives (skin moisturization), colorants, optical brighteners, sunscreens, alpha hydroxy acids, natural herbal extracts, and the like.

Production

For purposes herein, "tissue products" are those paper products comprising one or more creped cellulosic webs or plies. Cellulosic webs suitable for use in the product of this invention include those webs useful for facial tissues, bathroom tissues, table napkins and paper towels. This includes webs having basis weights of from about 5 to about 30 pounds per 2880 square feet. It also includes webs containing a substantial proportion of synthetic fibers as well as webs which are substantially solely made of cellulose papermaking fibers.

The anti-viral lotion composition may be applied to the tissue product by any of the methods known in the art such as gravure printing, flexographic printing, spraying, WEKO, slot die coating, or electrostatic spraying. The preferred application methods are rotogravure printing methods, such as disclosed in commonly assigned copending U.S. Ser. No. 60/174,087, "Germicidal Tissue Product Using Rotogravure Rolls", filed on Dec. 30, 1999, or in U.S. Pat. No. 5,665,426, issued to Krzysik et al., both of which are incorporated herein by reference in their entireties.

In one preferred method of making an anti-viral tissue product, the lotion composition includes one or more anti-viral organic acids, one more polyesters, and one or more oils and/or one or more waxes, and has a melting point from about 30° C. to about 70° C. The lotion composition is heated until it melts, and then is uniformly applied one or more surfaces of a tissue web in spaced-apart deposits. The composition is then resolidified by cooling. The tissue web may be cooled before or after the deposits of the coating composition are applied in order to accelerate solidification of the deposits.

Preferred lotion add-on is in the range of 1% to 40% of total tissue weight, more specifically from about 5 to about 25 weight percent, and still more specifically from about 10 to about 15 weight percent. The add-on amount will depend upon the desired effect of the composition on the product attributes and the specific composition.

The surface area coverage of the composition is preferably uniform over substantially all of the tissue surface, but only partially covers the surface(s) of the tissue product. This is achieved by a large number of small spaced-apart deposits which, when viewed by the naked eye, appear to cover the entire surface, but in fact do not. The actual surface area coverage of the deposits can be from about 30 to about 99 percent, more specifically from about 50 to about 80 percent. ("Surface area" is the area of a simple plan view of the tissue, not taking into account the three-dimensional topography of the tissue which would otherwise increase the surface area value for any given tissue sample). By providing a large number of very small deposits, the penetration of the composition can be more easily controlled to substantially remain on or near the surface of the tissue.

The invention will be further illustrated with reference to the following specific example. It is understood that the example is given by way of illustration and is not meant to limit the disclosure or the claims that follow.

EXAMPLE

An antiviral lotion composition having the following components was prepared:

| Component | Weight Percent |
|---|---|
| Water | 5.0 |
| Citric Acid | 1.0 |
| Methyl-1-Oleyl Amido Ethyl-2-Oleyl Imidazolinium Methyl Sulfate, 90% solids in propylene glycol | 2.0 |
| Lexorez TL-8 | 10.0 |
| Mineral Oil | 49.04 |
| Dimethicone, 100 cSt | 0.82 |
| Isopropyl Palmitate | 2.46 |
| Ceresin Wax | 14.76 |
| Stearyl Alcohol | 14.76 |
| Aloe Extract | 0.08 |
| Vitamin E Acetate | 0.08 |

The components were first grouped into two phases. Phase A contained the water, citric acid, methyl-1-oleyl amido ethyl-2-oleyl imidazolinium methyl sulfate, and Lexorez TL-8. Phase B contained the remaining components.

Phase A was prepared by adding the citric acid to the water, and the mixture was stirred until the citric acid dissolved. The methyl-1-oleyl amido ethyl-2-oleyl imidazolinium methyl sulfate was then added to the mixture and the new mixture was again stirred until dissolved. Finally, Lexorez TL-8 was added to the mixture, and the mixture was stirred until uniform.

Phase B was prepared by first adding the dimethicone to the isopropyl palmitate and stirring until the mixture was well dispersed. The mineral oil was heated to 60° C., and the dimethicone/isopropyl palmitate mixture was then added to the hot mineral oil and mixed until well dispersed. Ceresin wax was added to the batch and mixed until melted. Stearyl alcohol was then added to the batch and mixed until melted. The aloe extract and vitamin E acetate were then added and mixed until well dispersed.

With Phase B at a temperature of 60-65° C., Phase A was slowly added to Phase B with constant stirring. After thorough mixing, the composition was cooled to room temperature. The resulting composition was a uniform, soft, waxy, anti-viral solid, suitable for application to a tissue substrate.

It should be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention.

Accordingly, while the present invention has been described herein in detail in relation to several embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

We claim:

1. A non-irritating anti-viral lotioned tissue product having applied to at least one surface thereof an anti-viral lotion composition comprising:
   about 1% to about 25% of at least one anti-viral organic acid, said anti-viral organic acid comprising carboxylic acid having the structure R-COOH, wherein R is $C_1$–$C_6$ alkyl carboxyhydroxy;
   about 5% to about 25% of an emollient including at least one polyester, said polyester comprising trimethylpentanediol/adipic isononanoic acid copolymer; and
   a cationic surfactant.

2. A lotioned tissue product having applied to at least one surface thereof an anti-viral lotion composition comprising:
   about 1% to about 25% of at least one anti-viral organic acid, said anti-viral organic acid comprising carboxylic acid having the structure R-COOH, wherein R is $C_1$–$C_6$ alkyl carboxyhydroxy;
   about 5% to about 25% of an emollient including at least one polyester, said polyester comprising trimethylpentanediol/adipic acid copolymer; and
   a cationic surfactant.

3. The lotioned tissue product of claim 2, wherein said cationic surfactant comprises a quaternary ammonium compound.

4. A non-irritating, anti-viral lotion composition comprising:
   about 1% to about 25% of at least one anti-viral organic acid, said anti-viral organic acid comprising carboxylic acid having the structure R-COOH, wherein R is $C_1$–$C_6$ alkyl carboxyhydroxy;
   about 5% to about 25% of an emollient including at least one polyester, said polyester comprising trimethylpentanediol/adipic isononanoic acid copolymer; and
   a cationic surfactant.

5. A anti-viral lotion composition comprising:
   about 1% to about 25% of at least one anti-viral organic acid, said anti-viral organic acid comprising carboxylic acid having the structure R-COOH, wherein R is $C_1$–$C_4$ alkyl carboxyhydroxy;
   about 5% to about 25% of an emollient including at least one polyester, said polyester comprising trimethylpentanediol/adipic acid copolymer; and
   a cationic surfactant.

6. The lotion composition of claim 5, wherein said cationic surfactant comprises a quaternary ammonium compound.

7. A method of inhibiting the transfer of a viral infection comprising:
   providing anti-viral lotion tissue product having applied to at least one surface thereof an anti-viral lotion composition comprising about 1% to about 25% of at least one anti-viral organic acid, said anti-viral organic acid comprising carboxylic acid having the structure R-COOH, wherein R is $C_1$–$C_6$ alkyl carboxyhydroxy, about 5% to about 25% of an emollient including at least one polyester, said polyester comprising trimethylpentanediol/adipic acid copolymer, and a cationic surfactant;
   contacting a fluid containing at least one virus with said anti-viral tissue product; and
   absorbing said fluid within said absorbent article to contact the fluid with said anti-viral lotion composition.

8. The method of claim 7, further comprising:
   transferring a portion of the lotion composition to the user of the tissue product.

* * * * *

UNITED STATES PATENT AND TRADEMARK OFFICE
CERTIFICATE OF CORRECTION

PATENT NO. : 7,115,273 B2 Page 1 of 1
APPLICATION NO. : 09/753136
DATED : October 3, 2006
INVENTOR(S) : Shanklin et al.

It is certified that error appears in the above-identified patent and that said Letters Patent is hereby corrected as shown below:

On the title page,
item 45 and

[*] Notice: Subject to any disclaimer, the term of this patent is extended or adjusted under 35 USC 154(b) by (757) days Delete the phrase "by 757 days" and insert -- by 417 days--

Signed and Sealed this

Twenty-seventh Day of March, 2007

JON W. DUDAS
*Director of the United States Patent and Trademark Office*